(12) United States Patent
Marshall et al.

(10) Patent No.: US 8,372,103 B2
(45) Date of Patent: Feb. 12, 2013

(54) LANCET FIRING DEVICE

(75) Inventors: Jeremy Marshall, Jericho (GB); Mark Eaton, Witney (GB)

(73) Assignee: Owen Mumford, Ltd. (GB)

( * ) Notice: Subject to any disclaimer, the term of this patent is extended or adjusted under 35 U.S.C. 154(b) by 473 days.

(21) Appl. No.: 11/651,241

(22) Filed: Jan. 9, 2007

(65) Prior Publication Data

US 2007/0162063 A1   Jul. 12, 2007

(30) Foreign Application Priority Data

Jan. 12, 2006 (GB) .................. 0600523.5

(51) Int. Cl.
*A61B 17/32* (2006.01)
(52) U.S. Cl. ...................................... 606/181
(58) Field of Classification Search .............. 606/180, 606/118, 181, 182; 600/583
See application file for complete search history.

(56) References Cited

U.S. PATENT DOCUMENTS

| | | |
|---|---|---|
| 930,477 A | 8/1909 | Hudson |
| 3,620,209 A | 11/1971 | Kravitz |
| 3,659,608 A | 5/1972 | Perry |
| 3,698,395 A | 10/1972 | Hasson |
| 3,760,809 A | 9/1973 | Campbell |
| 4,442,836 A | 4/1984 | Melnecke et al. |
| 4,449,529 A | 5/1984 | Burns et al. |
| 4,462,405 A | 7/1984 | Ehrlich |
| 4,517,978 A | 5/1985 | Levin et al. |
| D281,383 S | 11/1985 | Beach |
| 4,553,541 A | 11/1985 | Burns |
| 4,565,545 A | 1/1986 | Suzuki |
| 4,646,753 A | 3/1987 | Nugent |
| 4,653,513 A | 3/1987 | Dombrowski |
| 4,820,287 A | 4/1989 | Leonard |
| RE32,922 E | 5/1989 | Levin et al. |
| 4,858,607 A | 8/1989 | Jordan et al. |
| 4,902,279 A | 2/1990 | Schmidtz et al. |
| 4,917,243 A | 4/1990 | Abrams et al. |
| 4,967,763 A | 11/1990 | Nugent et al. |
| 5,026,388 A | 6/1991 | Ingalz |
| 5,046,612 A | 9/1991 | Mostarda et al. |
| D322,211 S | 12/1991 | Gary |
| 5,104,380 A | 4/1992 | Holman et al. |
| 5,104,388 A | 4/1992 | Quackenbush |

(Continued)

FOREIGN PATENT DOCUMENTS

| | | |
|---|---|---|
| DE | 1049188 | 1/1959 |
| DE | 3730469 A1 | 6/1988 |

(Continued)

OTHER PUBLICATIONS

JP 2005185712A Shiga Moulding, WPI Abstract Accession No. 2005-464425 and EPO DOC Abstract.

(Continued)

*Primary Examiner* — S. Thomas Hughes
*Assistant Examiner* — Julie A Szpira
(74) *Attorney, Agent, or Firm* — Kilpatrick Townsend & Stockton LLP

(57) ABSTRACT

There is provided a lancet firing device comprising a projection, configured to project into an interior cavity of a lancet body when a lancet having a lancet body is loaded into the firing device; and means to grip an inner wall of the lancet body, the means being disposed on the projection.

6 Claims, 1 Drawing Sheet

U.S. PATENT DOCUMENTS

| | | |
|---|---|---|
| 5,116,353 A | 5/1992 | Green |
| D327,214 S | 6/1992 | Stuart |
| D327,321 S | 6/1992 | Russell et al. |
| 5,147,306 A | 9/1992 | Gubich |
| 5,201,324 A | 4/1993 | Swierczek |
| 5,226,895 A | 7/1993 | Harris |
| 5,226,896 A | 7/1993 | Harris |
| 5,242,421 A | 9/1993 | Chan et al. |
| 5,279,585 A | 1/1994 | Balkwill |
| 5,308,340 A | 5/1994 | Harris |
| 5,320,609 A | 6/1994 | Haber et al. |
| 5,324,303 A | 6/1994 | Strong et al. |
| 5,353,806 A | 10/1994 | Heinzelman et al. |
| 5,364,362 A | 11/1994 | Schulz |
| 5,368,047 A | 11/1994 | Suzuki et al. |
| 5,383,865 A | 1/1995 | Michel |
| 5,402,798 A | 4/1995 | Swierczek et al. |
| 5,423,847 A | 6/1995 | Strong et al. |
| 5,439,453 A | 8/1995 | Kashanchi |
| 5,439,473 A | 8/1995 | Jorgensen |
| D362,064 S | 9/1995 | Smick |
| 5,454,828 A | 10/1995 | Schraga |
| 5,472,433 A | 12/1995 | Suzuki |
| 5,487,748 A | 1/1996 | Marshall et al. |
| 5,514,097 A | 5/1996 | Knauer |
| 5,527,296 A | 6/1996 | Kashanchi |
| 5,529,581 A | 6/1996 | Cusack |
| 5,547,702 A | 8/1996 | Gleisner |
| 5,552,117 A | 9/1996 | Burns |
| 5,554,166 A | 9/1996 | Lange et al. |
| 5,569,286 A | 10/1996 | Peckham et al. |
| 5,580,794 A | 12/1996 | Allen |
| 5,591,136 A | 1/1997 | Gabriel |
| 5,601,588 A * | 2/1997 | Tonomura et al. ............ 606/185 |
| 5,609,577 A | 3/1997 | Haber et al. |
| 5,611,809 A * | 3/1997 | Marshall et al. .............. 606/181 |
| 5,613,978 A | 3/1997 | Harding |
| 5,626,566 A | 5/1997 | Petersen et al. |
| 5,628,764 A | 5/1997 | Schraga |
| 5,709,699 A | 1/1998 | Warner |
| 5,725,508 A | 3/1998 | Chanoch et al. |
| 5,730,753 A | 3/1998 | Morita |
| 5,743,889 A | 4/1998 | Sams |
| 5,749,886 A | 5/1998 | Abidin et al. |
| 5,797,942 A | 8/1998 | Schraga |
| 5,827,232 A | 10/1998 | Chanoch et al. |
| 5,837,546 A | 11/1998 | Allen et al. |
| 5,871,494 A | 2/1999 | Simons et al. |
| 5,872,713 A | 2/1999 | Douglas et al. |
| 5,879,311 A | 3/1999 | Duchon et al. |
| 5,879,367 A | 3/1999 | Latterell et al. |
| 5,910,147 A | 6/1999 | Rosenberg et al. |
| 5,916,230 A * | 6/1999 | Brenneman et al. .......... 606/172 |
| 5,951,493 A | 9/1999 | Douglas et al. |
| 6,004,297 A | 12/1999 | Steenfeldt-Jensen et al. |
| D421,214 S | 2/2000 | Koros et al. |
| 6,053,930 A | 4/2000 | Ruppert |
| 6,056,765 A | 5/2000 | Bajaj et al. |
| 6,071,249 A | 6/2000 | Cunningham et al. |
| 6,071,250 A | 6/2000 | Douglas et al. |
| 6,093,156 A | 7/2000 | Cunningham et al. |
| 6,106,539 A | 8/2000 | Fortier |
| 6,132,449 A | 10/2000 | Lum et al. |
| 6,136,013 A | 10/2000 | Marshall et al. |
| 6,152,942 A | 11/2000 | Brenneman et al. |
| 6,159,181 A | 12/2000 | Crossman et al. |
| 6,197,040 B1 | 3/2001 | LeVaughn et al. |
| 6,203,504 B1 | 3/2001 | Latterell et al. |
| 6,210,420 B1 | 4/2001 | Mauze et al. |
| 6,248,095 B1 | 6/2001 | Giambattista et al. |
| 6,261,245 B1 | 7/2001 | Kawai et al. |
| D446,107 S | 8/2001 | Carter |
| 6,277,097 B1 | 8/2001 | Klitmose et al. |
| 6,283,982 B1 | 9/2001 | LeVaughn et al. |
| 6,306,152 B1 | 10/2001 | Verdonk et al. |
| 6,319,209 B1 * | 11/2001 | Kriz ............. 600/583 |
| 6,332,871 B1 | 12/2001 | Douglas et al. |
| 6,419,661 B1 | 7/2002 | Kuhr et al. |
| 6,464,649 B1 | 10/2002 | Duchon et al. |
| 6,491,709 B2 | 12/2002 | Sharma et al. |
| D470,391 S | 2/2003 | Adams |
| 6,540,762 B1 * | 4/2003 | Bertling ........................ 606/182 |
| 6,558,402 B1 | 5/2003 | Chelak et al. |
| 6,589,210 B1 | 7/2003 | Rolfe |
| 6,607,508 B2 | 8/2003 | Knauer |
| 6,616,640 B2 * | 9/2003 | Chen ............................. 604/220 |
| 6,645,219 B2 | 11/2003 | Roe |
| 6,706,049 B2 | 3/2004 | Moerman |
| 6,755,805 B1 | 6/2004 | Reid |
| 6,899,698 B2 | 5/2005 | Sams |
| 6,899,699 B2 | 5/2005 | Enggaard |
| 6,902,554 B2 | 6/2005 | Huttner |
| 6,945,961 B2 | 9/2005 | Miller et al. |
| D516,218 S | 2/2006 | Larocca |
| 7,112,187 B2 | 9/2006 | Karlsson |
| D529,792 S | 10/2006 | Klein et al. |
| 7,241,278 B2 | 7/2007 | Moller |
| 7,244,266 B2 * | 7/2007 | Garthe et al. .................. 606/181 |
| 2002/0004196 A1 | 1/2002 | Whitson |
| 2002/0013602 A1 | 1/2002 | Huttner |
| 2002/0016606 A1 | 2/2002 | Moerman |
| 2002/0029058 A1 | 3/2002 | LeVaughn et al. |
| 2002/0082521 A1 | 6/2002 | Sharma et al. |
| 2002/0130042 A1 | 9/2002 | Moerman et al. |
| 2002/0169393 A1 | 11/2002 | Cunningham et al. |
| 2002/0198444 A1 | 12/2002 | Uchigaki et al. |
| 2003/0050655 A1 | 3/2003 | Roe |
| 2003/0195540 A1 | 10/2003 | Moerman |
| 2004/0098010 A1 | 5/2004 | Davison |
| 2004/0158271 A1* | 8/2004 | Hamamoto ................... 606/181 |
| 2004/0162573 A1 | 8/2004 | Kheiri |
| 2005/0038465 A1 * | 2/2005 | Shraga ........................ 606/182 |
| 2005/0197625 A1 | 9/2005 | Haueter et al. |
| 2006/0229652 A1* | 10/2006 | Iio et al. ....................... 606/182 |
| 2006/0259058 A1* | 11/2006 | Schiff et al. .................... 606/181 |
| 2007/0129687 A1 | 6/2007 | Marshall |
| 2007/0156163 A1 | 7/2007 | Davison et al. |
| 2007/0225742 A1 | 9/2007 | Abe et al. |
| 2007/0233166 A1 | 10/2007 | Stout |
| 2007/0299394 A1 | 12/2007 | Rolfe |
| 2008/0033469 A1* | 2/2008 | Winheim et al. .............. 606/181 |
| 2008/0306446 A1 | 12/2008 | Markussen |
| 2009/0054839 A1 | 2/2009 | Moller et al. |
| 2010/0004560 A1 | 1/2010 | Davison |
| 2010/0069845 A1 | 3/2010 | Marshall |
| 2010/0179485 A1 | 7/2010 | Radmer et al. |

FOREIGN PATENT DOCUMENTS

| | | |
|---|---|---|
| DE | 102004045043 | 4/2006 |
| EP | 0097748 | 1/1984 |
| EP | 0137975 A2 | 4/1985 |
| EP | 0295075 | 12/1988 |
| EP | 0327910 | 8/1989 |
| EP | 338806 | 10/1989 |
| EP | 0450905 | 10/1991 |
| EP | 0555554 A1 | 8/1993 |
| EP | 0783868 A1 | 7/1997 |
| EP | 897728 | 2/1999 |
| EP | 0925021 B1 | 6/1999 |
| EP | 0956874 | 11/1999 |
| EP | 1174083 | 1/2002 |
| EP | 1204371 A1 | 5/2002 |
| EP | 1507566 | 11/2003 |
| EP | 1570792 A1 | 9/2005 |
| EP | 1785090 | 5/2007 |
| EP | 1819382 | 8/2007 |
| FR | A2649893 | 1/1991 |
| GB | 2440119 A | 1/2008 |
| GB | 2465391 | 5/2010 |
| WO | WO85 04089 | 9/1985 |
| WO | WO 8808724 | 11/1988 |
| WO | WO91 08786 | 6/1991 |
| WO | WO 9110460 | 7/1991 |
| WO | WO 9607443 | 3/1996 |
| WO | WO97 04707 | 2/1997 |
| WO | WO97 08986 | 3/1997 |
| WO | WO 98/06331 | 2/1998 |

| | | |
|---|---|---|
| WO | WO 9906100 | 2/1999 |
| WO | WO 9938554 | 8/1999 |
| WO | WO 01/13794 A1 | 3/2001 |
| WO | WO01 28423 A2 | 4/2001 |
| WO | WO01 62150 A1 | 8/2001 |
| WO | WO 0172361 | 10/2001 |
| WO | WO01 95806 A2 | 12/2001 |
| WO | WO02 09575 A2 | 2/2002 |
| WO | WO 0230495 | 4/2002 |
| WO | WO02 053214 | 7/2002 |
| WO | WO 03/097133 A1 | 11/2003 |
| WO | WO 2004002556 | 1/2004 |
| WO | 2004082748 | 9/2004 |
| WO | WO2004 093940 A2 | 11/2004 |
| WO | 2005013825 A1 | 2/2005 |
| WO | 2005020816 | 3/2005 |
| WO | WO2006 045528 A1 | 5/2006 |
| WO | WO2006 045529 A1 | 5/2006 |
| WO | WO2006 450526 A1 | 5/2006 |
| WO | 2006058654 | 6/2006 |
| WO | WO 2006092309 A2 * | 9/2006 |
| WO | 2008009984 A1 | 1/2008 |
| WO | 2010055330 | 5/2010 |

OTHER PUBLICATIONS

Search Report in Priority Application No. GB0600523.5 dated Feb. 14, 2007.
Office Action dated Mar. 13, 2009 in related U.S. Appl. No. 11/712,754.
Office Action dated Dec. 30, 2008 in related U.S. Appl. No. 11/598,969.
Office Action dated Apr. 17, 2009 in related U.S. Appl. No. 11/598,969.
Office Action dated May 11, 2006 in related U.S. Appl. No. 10/635,806.
Response dated Oct. 10, 2006 in related U.S. Appl. No. 10/635,806.
Office Action dated Nov. 6, 2006 in related U.S. Appl. No. 10/635,806.
Response dated Jan. 5, 2007 in related U.S. Appl. No. 10/635,806.
Advisory Action dated Jan. 25, 2007 in related U.S. Appl. No. 10/635,806.
U.S. Appl. No. 09/959,262, filed Oct. 22, 2001.
Office Action dated Jul. 21, 2003 in related U.S. Appl. No. 09/959,262.
Response dated Oct. 14, 2003 in related U.S. Appl. No. 09/959,262.
Office Action dated Nov. 4, 2003 in related U.S. Appl. No. 09/959,262.
Owen Mumford Brochure entitled "AutojectMini" two pages (1993).
Owen Mumford Drawing No. AJ525, one page (1995).
Anapen® Patient Information Leaflet Celltech, two pages (2002).
Clexane® HandyPEN® Brochure Clexane 20, two pages (1999).
Serono Home Care list of contents and related invoice, two pages (2002).
Webpage ENBREL.ca: How to Use ENBREL SureClick Autoinjector: Introduction, five pages) accessed 2009 http://www.enbrel.ca/en/about/howUseSureClick/intro.html.
SimpleJect™ Auto-Inject System Directions for Use Brochure, 8 pages (2001).
SimpleJect™ Drawing #AJ/1700/11/0024/01, 3 pages (1999).
Owen Mumford Advanced New autoject2 Brochure, three pages (1995).
Knoll/Abbott Drawing DP321 and invoice, three pages (1999).
AMGEN Aranesp® Information Leaflet, two pages (2005).
'Blood Glucose Concentrations of Arm and Finger During Dynamic Glucose Conditions' by Ete Z. Szuts, Ph.D., *Diabetes Technology & Therapeutics*, 4(1):3-11 (2002).
'Vacuum-Assisted Lancing of the Forearm: An Effective and Less Painful Approach to Blood Glucose Monitoring' by David D. Cunningham, *Diabetes Technology & Therapeutics*, 2(4):541-548 (2000).
Ascensia® MICROLET® VACULANCE® Lancing Device; product information brochure; www.bayercarediabetes.com; printed Feb. 13, 2003 (03 pages).
Ascensia® MICROLET® VACULANCE® Lancing Device; product information brochure for Easy Lancing on Alternative Sites; www.bayercarediabetes.com; printed Feb. 13, 2004 (02 pages).
Glucose® Automatic Lancing Device / An Illustrated User Procedure, 02 pages (dateunknown).
Davis, Opening Up the Gate Control Theory, Nurs. Stand., 7(45)25-7 (1993).
Apkarian, et al., Heat-induced Pain Diminishes Vibrotactile Perception: A Touch Gate, Somatosens Mot. Res., 11(3):259-67 (1994).
Barnhill, et al., Using Pressure to Decrease the Pain of Intramuscular Injections, Journal of Pain and Symptom Management, 12:52-58 (1996), Published by Elsevier, New York, New York.
Office Action dated Apr. 27, 2011 in related U.S. Appl. No. 12/561,320.
International Search Report dated Feb. 19, 2010 in International Application No. PCT/GB2009/051510.
Search Report dated Oct. 13, 2009 in Application No. GB0820969.4.
Office Action dated Aug. 12, 2011 in U.S. Appl. No. 12/557,833.
Office Action dated Dec. 13, 2011 in U.S. Appl. No. 12/557,833.
Response dated Sep. 27, 2011 in U.S. Appl. No. 12/561,320.
Search Report dated Sep. 6, 2004 in Application No. GB0409354.8.
Office Action dated Jun. 7, 2012 in U.S. Appl. No. 12/561,320.
Ascensia®Microlet®Vaculance® Lancing Device; product information brochure for Easy Lancing on Alternative Sites; www.bayercarediabetes.com; printed Feb. 13, 2004 (02 pages).
At Last™ Blood Glucose System User's Manual, AMIRA, 35 pages ((c) 1999).
TheraSense™ The Technology of Caring Owner's Booklet, 35 pages (2000).
Davis, 'Opening Up the Gate Control Theory, Nurs. Stand., 7(45)25-7 (1993).
Apkarian, et al., 'Heat-induced Pain Diminishes Vibrotactile Perception: A Touch Gate, Somatosens Mot. Res., 11(3):259-67 (1994).
Melzack, 'From the Gate to the Neuromatrix,' Pain Supplement 6 S121-S126 (1999), Published by Elsevier Science B.V.
Barnhill, et al., 'Using Pressure to Decrease the Pain of Intramuscular Injections, Journal of Pain and Symptom Management, 12:52-58 (1996), Published by Elsevier, New York, New York.
Autopen™ Owen Mumford Ltd. Of Woodstock, UK, one page (May 7, 2007) http://www.owenmumford.com.
Office Action dated Nov. 7, 2012 in U.S. Appl. No. 13/495,316.

* cited by examiner

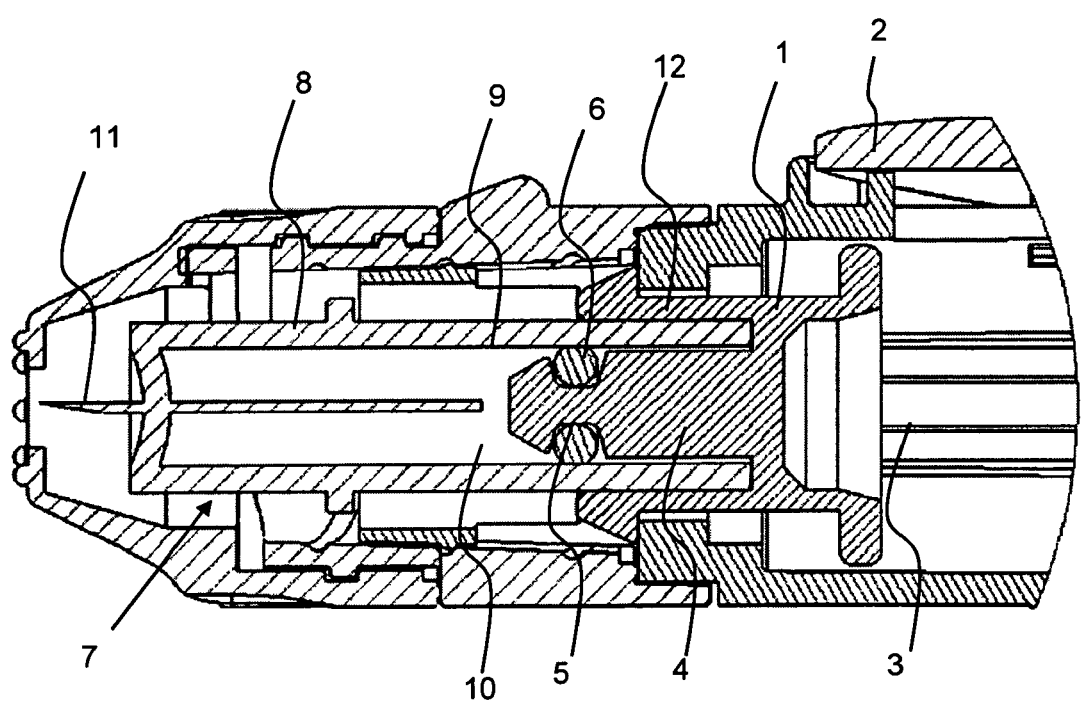

LANCET FIRING DEVICE

CROSS REFERENCE TO RELATED APPLICATION

This application claims priority to Great Britain Patent Application No. 0600523.5 filed on Jan. 12, 2006, the contents of which are incorporated herein by reference.

FIELD OF THE INVENTION

The present invention relates to lancet firing devices.

BACKGROUND TO THE INVENTION

Skin pricking lancets are well known in the art. Many such lancets comprise a needle having a sharp tip at one end and being embedded in a body at the opposite end, with the tip of the needle protruding from the body. Such lancets are used to obtain a small blood sample for analysis. Many lancet firing devices have been devised to make the procedure of skin pricking as simple and safe as possible. Such firing devices typically include a holder for holding the lancet body, and a firing mechanism. The firing mechanism is configured to push the needle of the lancet into the skin for a predetermined distance or using a predetermined force. An example of such a firing device is described in EP1204371.

The lancets themselves tend to be cheap, disposable items. Generally, they should not be reused. However, firing devices of the type described above tend to be reusable, and so the lancet holder is configured to allow an old lancet to be replaced by a new lancet. Firing devices of one manufacturer should, as far as possible, be useable with lancets produced by another manufacturer.

Lancet bodies are typically cylindrical in shape. The lancet holders commonly have a corresponding cylindrical socket into which the rear end of the lancet body can be pushed to secure the lancet within the holder. However, variations in the diameter of lancets between those supplied by one manufacturer and those supplied by another manufacturer, and even variations in the diameter of lancets from the same manufacturer can lead to problems in securing the lancet. For example, sometimes the lancets are secured too loosely, and other times the lancets are too large to fit into the cylindrical socket.

EP0925021 attempts to address this problem by providing a cylindrical socket with a split down the wall of the cylinder and a coil spring disposed around the wall to constrict the socket. If a lancet body has an external diameter slightly larger than the internal diameter of the socket, then the socket walls expand slightly to accommodate the larger lancet body, and are then constricted by the spring about the lancet body to hold it in place. However, this solution is not ideal if the lancet body is slightly too small. Furthermore, this solution is not ideal if the lancet body is not cylindrical but is another shape such as frustoconical.

SUMMARY OF THE INVENTION

According to a first aspect of the present invention, there is provided a lancet firing device comprising:
a projection, configured to project into an interior cavity of a lancet body when a lancet having a lancet body is loaded into the firing device; and
means to grip an inner wall of the lancet body, said means disposed on said projection.

One suitable means to grip an inner wall is an o-ring, the o-ring being disposed around the projection. Where an o-ring is used, it is preferred that the projection comprises a depression in its surface, the depression configured to receive the o-ring.

It is preferred that the lancet firing device further comprises a supporting wall configured to contact an outer surface of the lancet body. Ideally, the supporting wall is configured to form a friction fit with the lancet body.

BRIEF DESCRIPTION OF THE DRAWINGS

FIG. 1 shows a side elevation cutaway cross-section view of an end of a firing device with a lancet holder and lancet in place.

DETAILED DESCRIPTION OF AN EMBODIMENT

The firing device is in many respects similar to the firing device described in EP1204371. A lancet holder 1 of a firing device 2 is disposed in the firing device 2 at the end of a rod 3 that urges the lancet holder 1 to the left as illustrated when the firing device 2 is activated by a user.

The lancet holder 1 comprises a projection 4. The projection 4 is substantially cylindrical and comprises a depression 5 formed around it part-way along the length of the projection 4. An o-ring 6 is seated in the depression 5. The o-ring is formed from a compressible material that can be compressed and will spring back to its original shape. It is preferred that the o-ring material has a high coefficient of friction. A suitable material that has both of these desired properties is rubber.

The lancet holder 1 is configured to hold a cylindrical lancet 7. The lancet has a generally cylindrical outer wall 8, which has an inner surface 9 and defines a cavity 10 within the lancet 7. The lancet 7 further comprises a needle 11 for pricking skin. The needle 11 is disposed at one end of the lancet, and at the opposite end of the lancet 7 is an opening into the cavity 10.

In order to secure the lancet 7 to the lancet holder 1, the lancet 7 is pushed towards the lancet holder 1 such that the projection 2 enters the cavity 10 within the lancet 7. As the lancet 7 is pushed onto the projection, the o-ring 6 compresses against the inner wall 9 of the lancet 7. Once the lancet 7 is fully seated on the holder 1, the o-ring 6 grips the inner wall 9 of the lancet 7 firmly, thereby holding it in place. By gripping the lancet on an inner surface rather than an outer surface, lancets of different dimensions and different shapes can be gripped.

The outer surface of the lancet may or may not contact the inner surface of a supporting wall 12 formed as part of the lancet holder 1. The supporting wall 12 can ensure that the lancet body 8 is loaded into the firing device at the desired orientation. Furthermore, if the dimensions of the lancet body 8 and the supporting wall 12 are sufficiently close, the supporting wall 12 can provide a friction fit to further secure the lancet body onto the lancet holder 1.

It will be appreciated by those of skill in the art that various modifications may be made to the above described embodiment without departing from the scope of the present invention. For example, the means to grip an inner wall of the lancet body may include any suitable means, such as a mechanical clip or biasing means such as a spring.

We claim:

1. A lancet firing device suitable for firing skin pricking lancets, each lancet comprising a needle embedded within an enclosed end of a tubular lancet body, the device comprising:
a substantially cylindrical projection configured to project through an open end of the tubular lancet body into an interior cavity of the lancet body when the lancet is loaded into the firing device;

compressible means to grip an inner wall of the lancet body, said compressible means mounted on said projection; and a tubular supporting wall encircling the projection and configured to define a slot between the projection and the supporting wall into which the tubular lancet body can be loaded.

2. The lancet firing device as claimed in claim 1, wherein said compressible means to grip an inner wall comprises an o-ring.

3. The lancet firing device as claimed in claim 2, further comprising a depression in a surface of the projection, the depression configured to receive the o-ring.

4. A lancet firing device comprising:
 (a) a rod;
 (b) an o-ring;
 (c) a substantially cylindrical projection configured to secure a lancet to the lancet firing device, the lancet comprising a needle embedded within an enclosed end of a tubular lancet body, the lancet body having an interior cavity, an opening to the interior cavity, and an interior surface within the interior cavity, wherein the projection comprises:
  (i) a first end having a depression configured to receive the o-ring; and
  (ii) a second end coupled to the rod; and
 (d) a supporting wall that is configured to define a slot between the projection and the supporting wall into which the tubular lancet body can be loaded,
wherein the first end of the projection is configured to enter through the opening and into the interior cavity of the lancet body, the o-ring engaging the interior surface of the lancet body to secure the lancet to the firing device, and the supporting wall contacting an outer surface of the lancet body to form a friction fit with the lancet.

5. The lancet firing device as claimed in claim 1, further comprising a supporting wall configured to contact an outer surface of the lancet body.

6. The lancet firing device as claimed in claim 5, wherein the supporting wall is configured to form a friction fit with the lancet body.

* * * * *